US009027452B2

(12) United States Patent
Nagy et al.

(10) Patent No.: US 9,027,452 B2
(45) Date of Patent: May 12, 2015

(54) JAB SAW ACCESSORY TOOL FOR AN OSCILLATING TOOL

(75) Inventors: Balazs Nagy, Arlington Heights, IL (US); Jonathan Markwald, Elmhurst, IL (US); Edward Abante, Chicago, IL (US); Michael Landt, Chicago, IL (US); Saad Alam, Franklin Park, IL (US); Timothy Baker, Aurora, IL (US); Joshua Barhitte, Chicago, IL (US); Peter Denley, Huntersville, NC (US)

(73) Assignee: Robert Bosch GmbH, Stuttgart (DE)

( * ) Notice: Subject to any disclaimer, the term of this patent is extended or adjusted under 35 U.S.C. 154(b) by 402 days.

(21) Appl. No.: 13/337,377

(22) Filed: Dec. 27, 2011

(65) Prior Publication Data

US 2013/0160631 A1 Jun. 27, 2013

(51) Int. Cl.
  *B23D 61/06* (2006.01)
  *B23D 61/00* (2006.01)
  *A61B 17/128* (2006.01)

(52) U.S. Cl.
  CPC ............. *B23D 61/006* (2013.01); *A61B 17/128* (2013.01)

(58) Field of Classification Search
  CPC ........ B23D 61/006; B26B 7/00; A61B 17/14; A61B 17/141; A61B 17/148
  USPC ........... 83/523, 524, 544, 578, 821, 835, 846, 83/663, 665, 666, 698.11, 697; 30/346.61, 30/355, 392, 166.3, 348, 351
  See application file for complete search history.

(56) References Cited

U.S. PATENT DOCUMENTS

| 1,968,160 | A | * | 7/1934 | Nicholls | ............................ 7/132 |
| 2,232,940 | A | * | 2/1941 | Fender | ............................. 30/278 |
| 2,232,941 | A | * | 2/1941 | Fender | .......................... 30/279.6 |
| 2,795,045 | A | * | 6/1957 | Taylor | .............................. 30/314 |
| 2,801,640 | A | * | 8/1957 | Steele | ........................... 132/75.4 |
| 2,895,516 | A |   | 7/1959 | Mayer | |
| 4,513,742 | A | * | 4/1985 | Arnegger | ....................... 606/178 |
| 4,543,720 | A | * | 10/1985 | Grunikiewicz et al. | ....... 30/277.4 |
| 4,870,757 | A |   | 10/1989 | Kirkpatrick et al. | |
| 4,890,387 | A | * | 1/1990 | Canino | .............................. 7/118 |
| 5,038,478 | A | * | 8/1991 | Mezger et al. | ................ 30/272.1 |
| 5,178,626 | A | * | 1/1993 | Pappas | ........................... 606/178 |

(Continued)

FOREIGN PATENT DOCUMENTS

| DE | 19613538 C1 | 7/1997 |
| DE | 19932248 A1 | 1/2001 |

OTHER PUBLICATIONS

Fein Diamond Coated Sickle Saw Blade for SuperCut (data from Toolking.com website downloaded Mar. 11, 2011).

(Continued)

*Primary Examiner* — Sean Michalski
(74) *Attorney, Agent, or Firm* — Maginot Moore & Beck LLP

(57) ABSTRACT

An accessory for a power tool, includes a mounting portion configured to mate with an oscillating drive member of a power tool. A support arm portion extends from the mounting portion in a first direction. The support arm portion includes an inner edge that faces in a second direction transverse to the first direction. A blade portion extends from the support arm generally in the second direction. The blade portion includes a trailing edge arranged facing generally toward the mounting portion and a leading edge arranged facing generally away from the mounting portion. The trailing edge and the leading edge portion meet to define a pointed tip portion.

6 Claims, 7 Drawing Sheets

(56) References Cited

U.S. PATENT DOCUMENTS

| | | | |
|---|---|---|---|
| 5,265,340 A * | 11/1993 | Nitz et al. | 30/166.3 |
| 5,295,426 A | 3/1994 | Planchon | |
| 5,448,833 A | 9/1995 | Coon | |
| 5,456,011 A * | 10/1995 | Inkster | 30/293 |
| 5,697,835 A * | 12/1997 | Nitz et al. | 451/548 |
| 5,735,866 A * | 4/1998 | Adams et al. | 606/178 |
| 5,947,805 A * | 9/1999 | Van Osenbruggen | 451/358 |
| 5,964,039 A * | 10/1999 | Mizoguchi et al. | 30/392 |
| 6,098,292 A * | 8/2000 | Harpell | 30/172 |
| 6,178,645 B1 * | 1/2001 | Lock | 30/275.4 |
| 6,401,342 B1 * | 6/2002 | Kloss et al. | 30/272.1 |
| 6,401,585 B1 * | 6/2002 | Morgan | 83/835 |
| 6,422,110 B1 * | 7/2002 | Wurst et al. | 76/104.1 |
| 6,601,306 B1 | 8/2003 | Lombardi | |
| 2001/0039738 A1 | 11/2001 | Bachta | |
| 2002/0014012 A1 | 2/2002 | Hoffman | |
| 2002/0104421 A1 * | 8/2002 | Wurst | 83/835 |
| 2004/0221461 A1 * | 11/2004 | Knisley et al. | 30/392 |
| 2005/0022390 A1 | 2/2005 | Whitemiller et al. | |
| 2006/0015117 A1 * | 1/2006 | Haines | 606/88 |
| 2006/0123959 A1 * | 6/2006 | Bocast | 83/13 |
| 2006/0272468 A1 * | 12/2006 | Gupta et al. | 83/835 |
| 2006/0277761 A1 | 12/2006 | Hagan et al. | |
| 2007/0209217 A1 * | 9/2007 | Ritter et al. | 30/392 |
| 2008/0229590 A1 | 9/2008 | Garrett | |
| 2008/0235955 A1 | 10/2008 | Rosso et al. | |
| 2012/0198709 A1 * | 8/2012 | Inkster | 30/503.5 |
| 2012/0255417 A1 * | 10/2012 | Frueh et al. | 83/835 |
| 2013/0174701 A1 * | 7/2013 | Elliston et al. | 83/34 |
| 2013/0269499 A1 * | 10/2013 | Bozic | 83/697 |
| 2013/0269963 A1 * | 10/2013 | Fuchs | 173/162.1 |
| 2013/0331013 A1 * | 12/2013 | Neal et al. | 451/461 |
| 2014/0018811 A1 * | 1/2014 | Mootien et al. | 606/82 |
| 2014/0082948 A1 * | 3/2014 | Staub | 30/355 |
| 2014/0190328 A1 * | 7/2014 | Karlen | 83/853 |
| 2014/0230626 A1 * | 8/2014 | Puzio et al. | 83/697 |
| 2014/0325855 A1 * | 11/2014 | Bozic | 30/392 |

OTHER PUBLICATIONS

International Search Report in correspondence PCT application (i.e., PCT/US2012/071027), mailed Apr. 11, 2013 (10 pages).

* cited by examiner

JAB SAW ACCESSORY TOOL FOR AN OSCILLATING TOOL

TECHNICAL FIELD

This invention relates to the field of oscillating power tools, and more particularly to accessory tools for use with oscillating power tools.

BACKGROUND

Oscillating power tools are lightweight, handheld tools configured to oscillate various accessory tools and attachments, such as cutting blades, sanding discs, grinding tools, and many others. The accessory tools enable the oscillating power tool to be used to shape and contour workpieces in a wide variety of ways. Previously known accessory tools, however, are limited in their ability to start and perform cuts in interior portions of drywall panels, wallboards, plaster boards, soft wood panels, and the like. For example, many home and do-it-yourself projects require that holes be cut into the middle of drywall panels for various reasons, such as drywall repair and mounting plugs, switches, ceiling fans, and the like.

Traditionally, cuts in the interior portions of the drywall panel are started using a penetrating tool, such as the sharp tip of a jab saw or a drill bit. Accessory tools for oscillating power tools, however, are generally incapable of being plunged through a drywall panel or soft wood panel to start a cut. Therefore, performing cuts in the interior portions of a drywall panel typically requires the use of a separate tool to start the cut. In addition, cutting holes into drywall panels often require that multiple small cuts be performed at different angles to form the holes. Because accessory tools for oscillating power tools generally have a single cutting edge, the oscillating tool must be oriented in different directions to perform the different cuts. In some cases, however, the operators ability to reorient the oscillating tool in different directions may be limited.

What is needed is an accessory tool for a handheld oscillating power tool that enables drywall cutting operations to be performed without requiring the use of a separate tool for starting the cut and that enables cuts to be performed in multiple directions without having to reorient the oscillating power tool.

SUMMARY

In accordance with one embodiment of the present disclosure, an accessory for a power tool, includes a mounting portion configured to mate with an oscillating drive member of a power tool. A support arm portion extends from the mounting portion in a first direction. The support arm portion includes an inner edge that faces in a second direction transverse to the first direction. A blade portion extends from the support arm generally in the second direction. The blade portion includes a trailing edge arranged facing generally toward the mounting portion and a leading edge arranged facing generally away from the mounting portion. The trailing edge and the leading edge portion meet to define a pointed tip portion.

In accordance with another embodiment, an accessory for an oscillating power tool includes a mounting portion configured to mate with an oscillating drive member of a power tool. A support arm portion extends from the mounting portion in a first direction. The support arm portion includes an inner edge that faces in a second direction transverse to the first direction. A blade portion extends from the support arm portion generally in the second direction. The blade portion includes a sharp tip portion oriented generally in the second direction and a trailing cutting edge arranged facing generally toward the mounting portion.

DESCRIPTION

Figure 1:
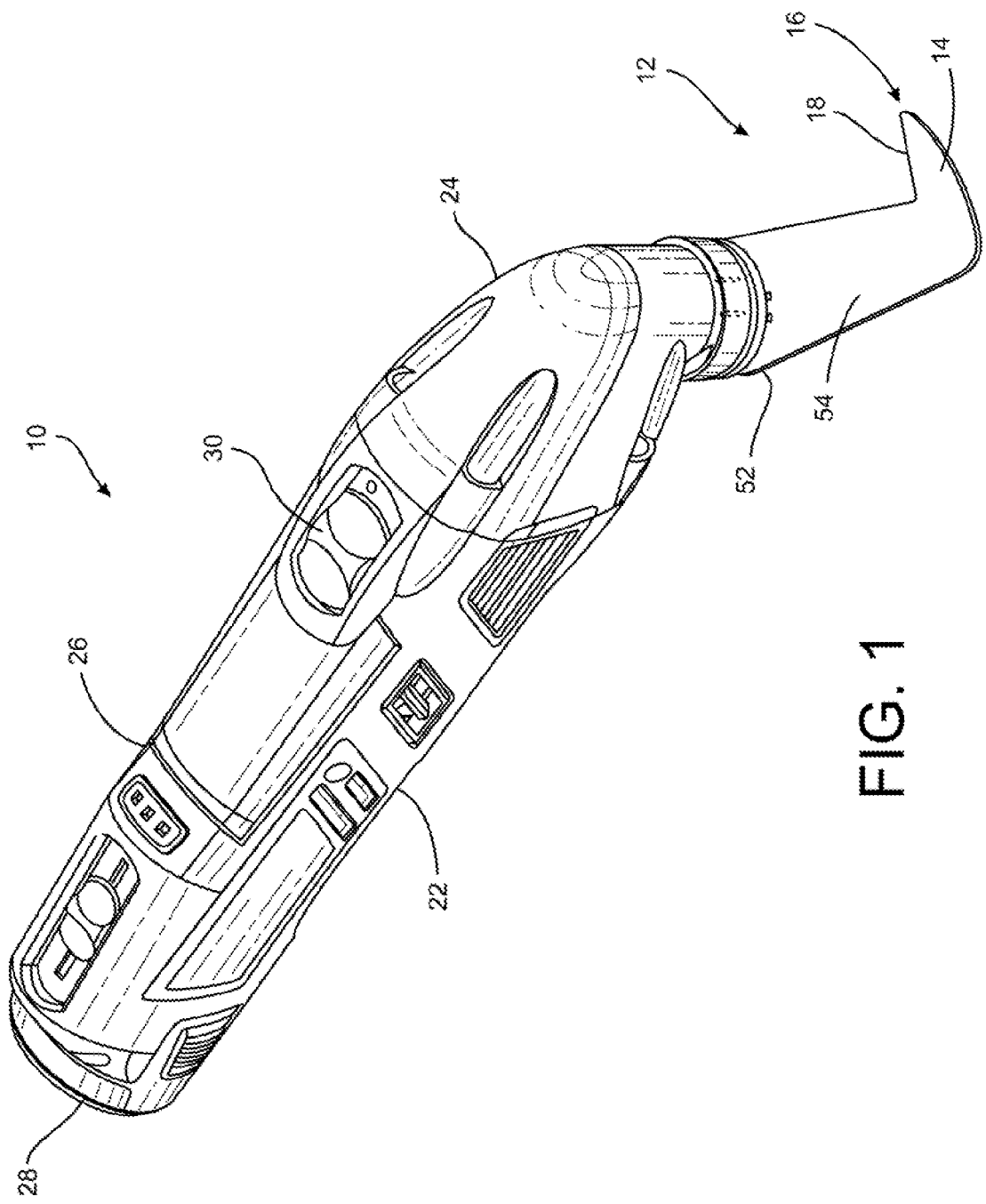
FIG. 1 is a perspective view of an oscillating tool including a jab saw accessory tool according to one embodiment the present disclosure.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one of ordinary skill in the art to which this invention pertains.

Referring to FIG. 1, the present disclosure is directed to a jab saw accessory tool 12 for an oscillating power tool 10. The jab saw accessory tool 12 facilitates using the oscillating power tool 10 in penetrating and cutting drywall and softer wood panels. The jab saw accessory tool 12 includes a mounting portion 52, a support arm portion 54, and a blade portion 14. The mounting portion 52 secures the accessory tool 12 to the oscillating tool 10. The support arm extends from the mounting portion 52 in a first direction. The blade portion 14 extends from the outer end of the support arm portion 54 in a second direction that is transverse to the first direction. The blade portion includes a penetrating tip 16 and a rearward facing cutting edge 18 that extends between the tip 16 and the support arm portion 54. The tip 16 enables the blade 14 to be plunged through drywall to start cuts. The rearward facing cutting edge 18 enables "pull" cutting using the oscillating power tool 10.

The oscillating tool 10 for driving the jab saw accessory includes a generally cylindrically shaped housing 22 constructed of a rigid material such as plastic, metal, or composite materials such as a fiber reinforced polymer. The housing 22 includes a nose portion 24 and a handle portion 26. The handle portion 26 encloses a motor (not shown). In one embodiment, the motor comprises an electric motor configured to receive power from a rechargeable battery 28 connected at the base of the handle portion 26. In other embodiments, electric power for the motor may be received from an AC outlet via a power cord (not shown). As an alternative to electric power, the oscillating power tool 10 may be pneumatically or hydraulically powered. Power to the motor is controlled by a power switch 40 provided on the handle portion 26 of the housing 22.

Figure 2:
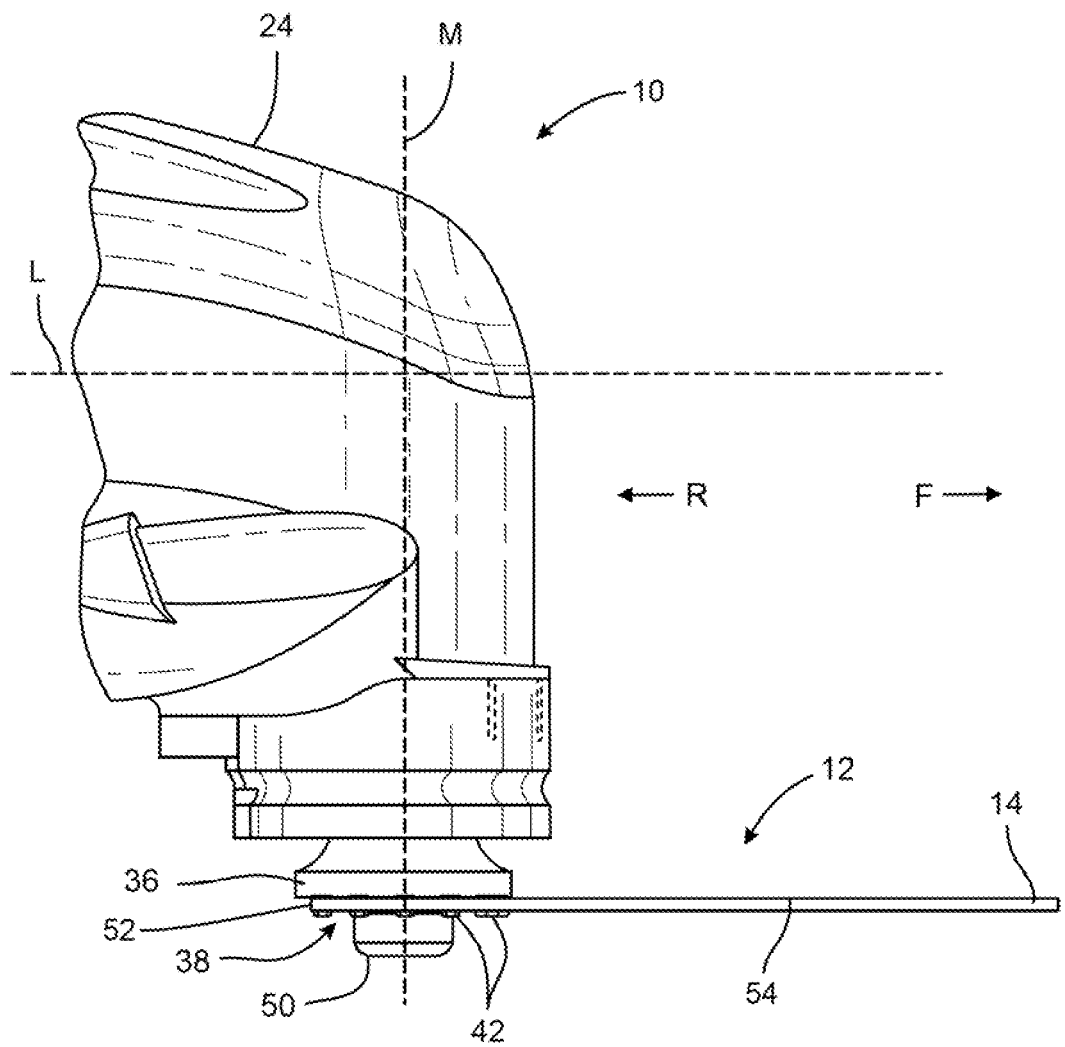
FIG. 2 is a side view of the nose portion of the oscillating tool and the jab saw accessory tool of FIG. 1.

Referring now to FIG. 2, the oscillating tool 10 defines a longitudinal axis L. An oscillating drive member (not shown) extends generally perpendicularly with respect to the longitudinal axis L. The motor is configured to oscillate the drive member about an axis M at high frequencies, e.g., 5,000 to 25,000 oscillations per minute, with a small oscillating angle, typically in a range of between 0.5° and 7°. The drive member supports an accessory tool holder 36 exterior to the housing 22. The tool holder 36 is configured to releasably secure various accessory tools to the drive member, such as the jab saw accessory tool 12. As the tool holder 36 is oscillated by the drive member 32, the accessory tool 12 is driven to oscillate about the axis M of the drive member 32.

To enable a secure connection between the tool holder 36 of the power tool 10 and accessory tools for use with the power tool, the tool holder 36 and associated accessory tools are provided with drive structures 38, 40 that mate to secure the accessory tool to the tool holder 36. In the embodiments described herein, the tool holder 36 includes a tool drive structure 38 that comprises a plurality of protrusions 42 arranged in a circular pattern about a central bore (not shown).

Figure 3:
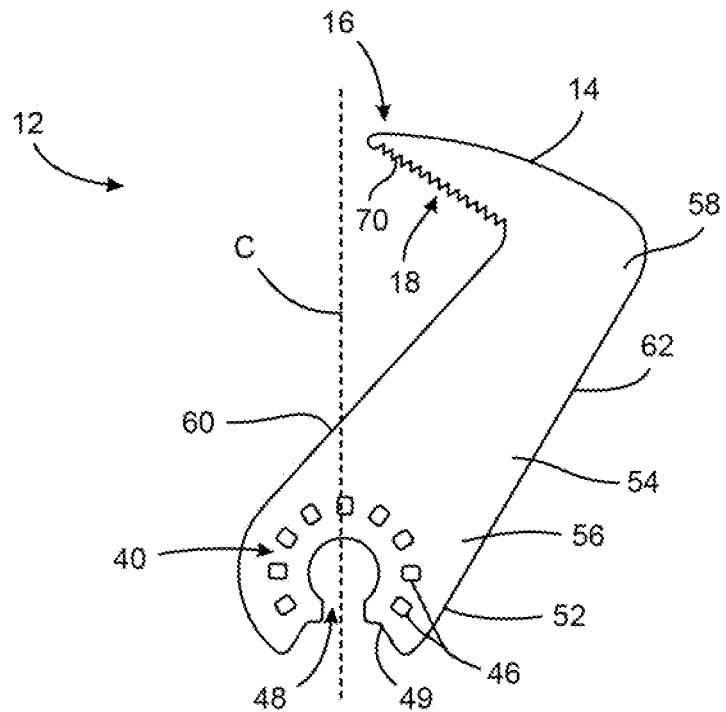
FIG. 3 is a top elevational view of the jab saw accessory tool of FIG. 1.

Accessory tools for use with the power tool 10, such as the jab saw accessory tool 12, include an accessory drive structure 40 that is configured to mate or interlock with the tool drive structure 38 of the tool holder 36. As depicted in FIG. 3, the accessory drive structure 40 of the accessory tool 12 includes a plurality of openings or recesses 46 and a central opening 48 that are sized, shaped, and positioned complementary to the protrusions 42 and central bore, respectively, of the tool drive structure 38. When the accessory tool 12 is placed onto the tool holder 36, the protruding features 42 of the tool drive structure 38 are received in the corresponding openings and/or recesses 46 defined in the accessory drive structure 40.

A clamping member 50 (FIG. 2), such as a clamping screw, is used to press the accessory drive structure 40 of the accessory tool 12 into interlocking engagement with the tool drive structure 38 thus securing the accessory tool 12 to the tool holder 36. The interlocked drive structures 38, 40 enable the oscillating movement of the tool holder 36 to be imparted to the accessory tool 12.

The jab saw accessory tool 12 comprises a planar body formed of a hard metal material, such as carbon steel. The jab saw accessory tool 12 may be formed by stamping sheet metal with one or more dies that define the perimeter shape and openings of the tool. As depicted, the body is shaped to form a mounting portion 52, a support arm portion 54, and a cutting blade portion 14.

The mounting portion 52 has a generally flat disc-like shape that defines the central opening 48 and smaller openings 46 of the accessory drive structure 40. As depicted in FIG. 3, the mounting portion defines a slot 49 that extends from the central opening through the outer periphery of the mounting portion 52. The slot 49 enables the mounting portion to be installed and removed from the tool holder 36 without having to completely remove the clamping screw 50. The mounting portion 52 defines a central axis C that is centered in the slot 49 and central opening 48. The central axis C of the mounting portion 52 defines the default mounting orientation of the accessory tool 12 and serves as a guide for mounting the accessory tool 12 to the tool holder 36 of the oscillating tool 10. In the default mounting orientation, the mounting portion 52 is secured to the tool holder 36 with the central axis C aligned with the longitudinal axis L of the oscillating tool 10. The mounting portion 52, however, can be secured to the tool holder 36 with the central axis C oriented in a plurality of different directions that are transverse to the longitudinal axis L. The mounting portion 40 is secured to the tool holder 36 with the body of the accessory tool arranged substantially perpendicular to the axis M (FIG. 2) of the drive member. The planar body thus oscillates substantially in a first plane, or oscillation plane, that is perpendicular to the axis M of the drive member.

The support arm 54 of the accessory tool comprises a beam cantilevered from the mounting portion 52 and extending from the mounting portion 52 generally in the forward direction F. The support arm 54 includes an inner end portion 56 adjacent the mounting portion 52 and an outer end portion 58 that is located distally with respect to the mounting portion 52. The support arm 54 also includes an inner lateral edge 60 and an outer lateral edge 62. The blade 14 of the accessory tool 12 extends generally laterally from the outer end portion 58 in a second direction that is transverse to the forward direction F. The blade 14 includes a leading edge, or forward facing edge, portion 66 and a trailing edge, or rearward facing edge, portion 18. The leading edge portion 66 and trailing edge portion 18 extend from the support arm portion 54 and meet to define the tip portion 16 as well as the general shape of the blade. As best seen in FIG. 3, the tip portion 16 of the blade tapers to a narrow, rounded point so the tip portion 16 can be used to penetrate drywall panels. In alternative embodiments, the tip portion 16 may be sharpened, e.g., by grinding, to facilitate penetration.

In the embodiment of FIGS. 1-3, the rearward facing cutting edge 18 of the blade 14 comprises a serrated cutting edge having a plurality of cutting teeth 70. The cutting teeth 70 may be formed in any suitable manner including grinding or laser cutting. The geometry of the cutting teeth can be varied to facilitate the cutting of different kinds of drywall or soft wood materials.

The support arm 54 offsets the blade 14 from the mounting portion 52 so the blade, and particularly the cutting edge 18, can be arranged generally parallel to the directions of oscillating movement of the drive member. The rear facing cutting edge 18 enables the jab saw accessory tool 12 to be used for "pull" cutting by pulling the oscillating tool 10 generally in the rearward direction R so the rear facing cutting edge 18 cuts into an edge of the drywall.

To facilitate cutting along the surface of a drywall member, the inner edge portion 60 of the support arm 54 can be used as a guide surface for the accessory tool 12. The inner edge portion 60 can be positioned in contact with the surface of a drywall panel that is being cut as the cutting edge 18 is being pulled through the drywall. As depicted in FIG. 3, the support arm portion 54 extends from the mounting portion 52 at an angle that is offset from the central axis C of the mounting portion 52 resulting in the inner edge portion 60 of the support arm 54 being intersected by the central axis C. When the accessory tool 12 is secured to the oscillating tool 10 in the default mounting orientation, the inner edge 60 is positioned in generally in front of the body of the oscillating tool at an angle with respect to the longitudinal axis L of the oscillating tool 10. This orientation allows the oscillating tool 10 extend away from the surface of the drywall when the inner edge portion is positioned in contact the drywall so the tool 10 can be easily held in clearance from the drywall while performing cuts.

Figure 4:
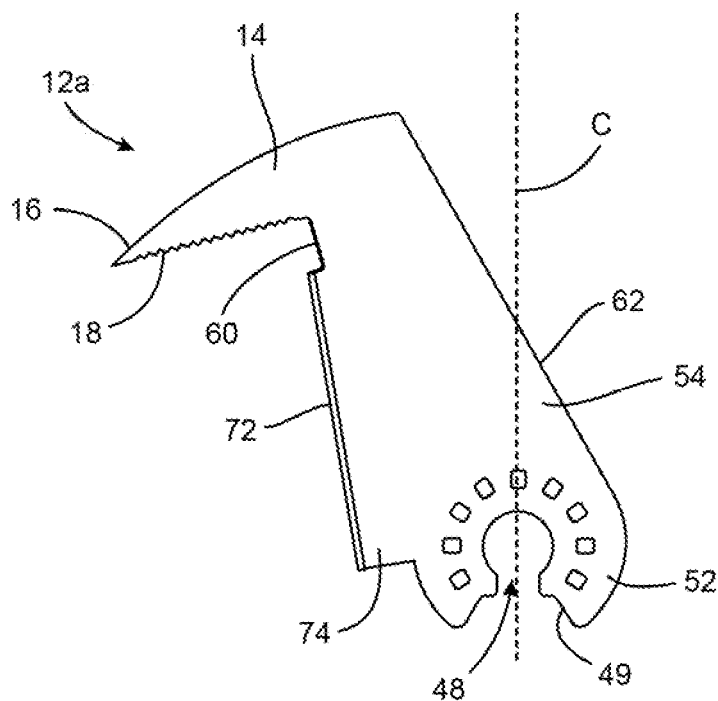
FIGS. 4-11 depict alternative embodiments of jab saw accessory tools for use with the oscillating tool of FIG. 1.
Figure 5:
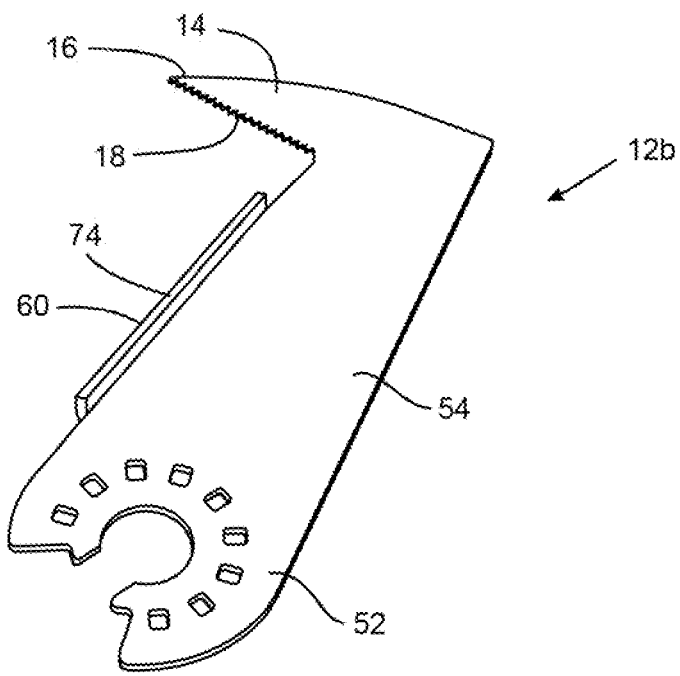
Figure 6:
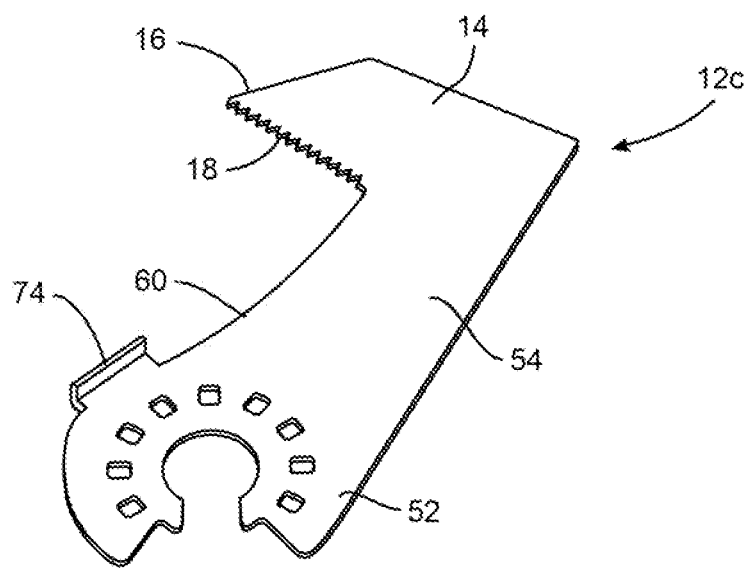
Figure 7:
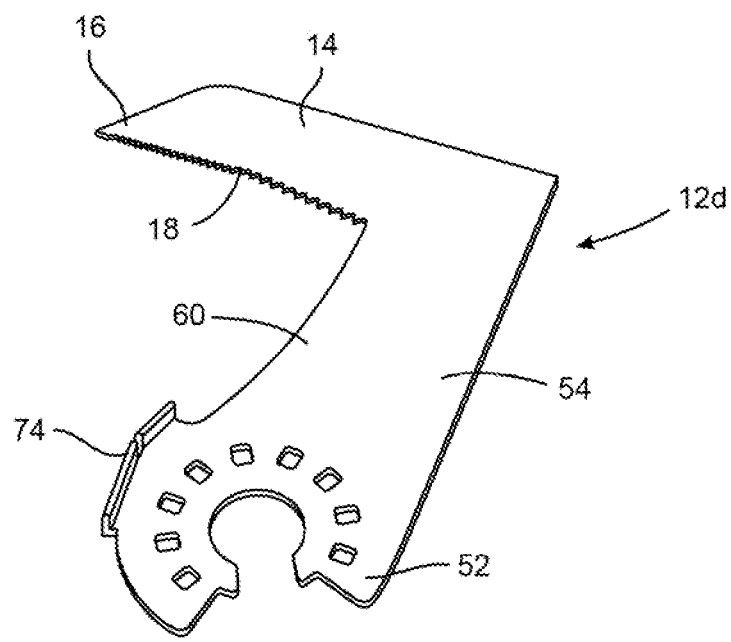
Figure 8:
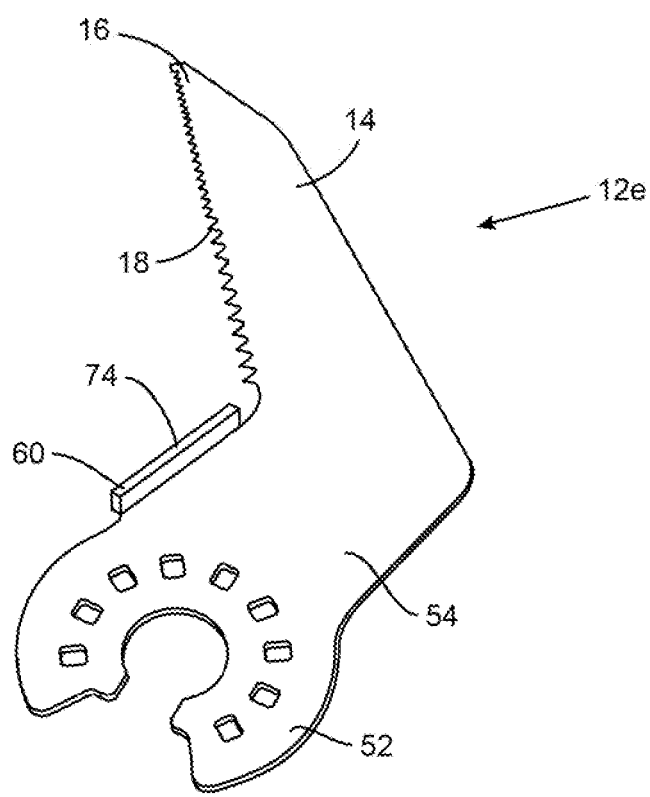
Figure 9:
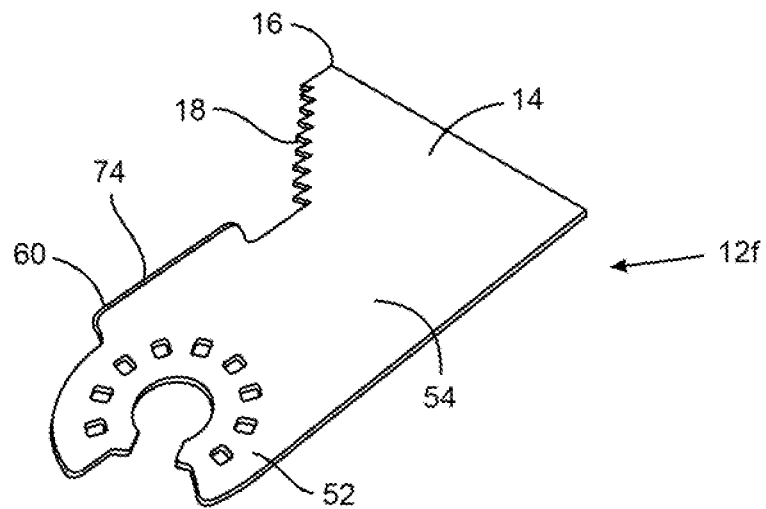
Figure 10:
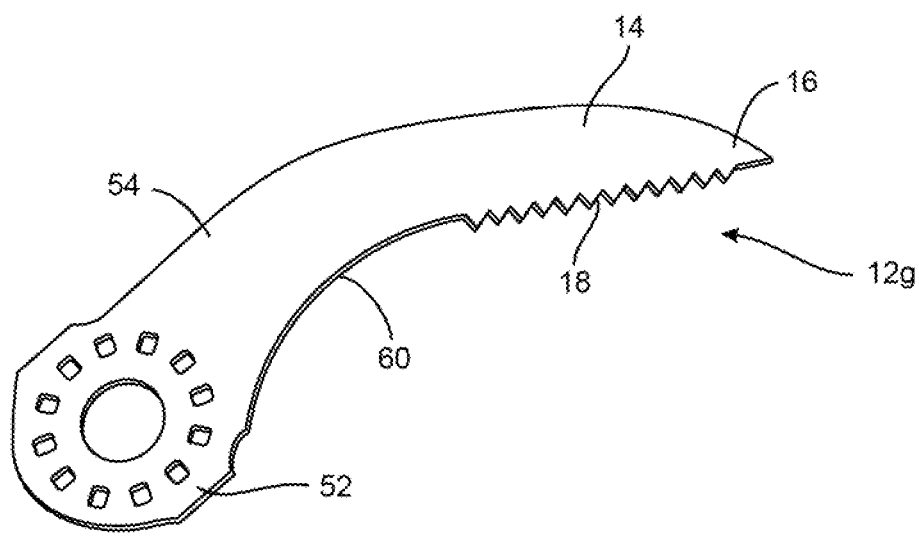

An embodiment of a jab saw accessory tool 12a is depicted in FIG. 4 that includes an alternative configuration of the inner edge 60. As depicted in FIG. 4, the inner edge 60 of the support arm 54 includes a guide edge portion 74. The guide edge portion 74 includes a lip portion 72 that is formed by bending the outer portion of the guide edge 74. The lip portion 72 provides a wider surface for use as the guide surface of the accessory tool 12. As depicted in FIG. 4, the guide edge portion 74 is offset outwardly from the inner edge 60 and the mounting portion 52 which enables an alternative default mounting orientation. In FIG. 4, the support arm portion 54 extends at an angle relative to the central axis C of the mounting portion that results in the tip portion 16 and blade portion 14 of the accessory tool 12a being positioned farther away from the central axis C than the rest of the accessory tool. The guide edge portion 74 is offset outwardly from the inner edge 60 and the mounting portion 52 to provide more clearance for oscillating tool to be held adjacent to a surface of a drywall panel when the guide surface 72 is positioned in contact with the drywall FIGS. 4-10 depict alternative embodiments of jab saw accessory tools 12a-12f that show alternative configurations of the support arm 54, blade portion 14, and tip portion 16. FIG. 5 depicts an embodiment of a jab saw accessory tool having an inner edge 60 that include a guide lip 74 that is not offset from the inner edge 60. FIGS. 6 and 7 depict embodiments jab saw accessory tool in which a guide lip 74 is provided on the mounting portion 52. In the embodiment of FIGS. 1-3, the guide surface 72 is arranged substantially perpendicular to the trailing cutting edge 18. FIGS. 8-10 depict embodiments jab saw accessory tools with blade portions 14 and cutting edges 18 provided at obtuse angles relative to the inner edge 60.

Figure 11:
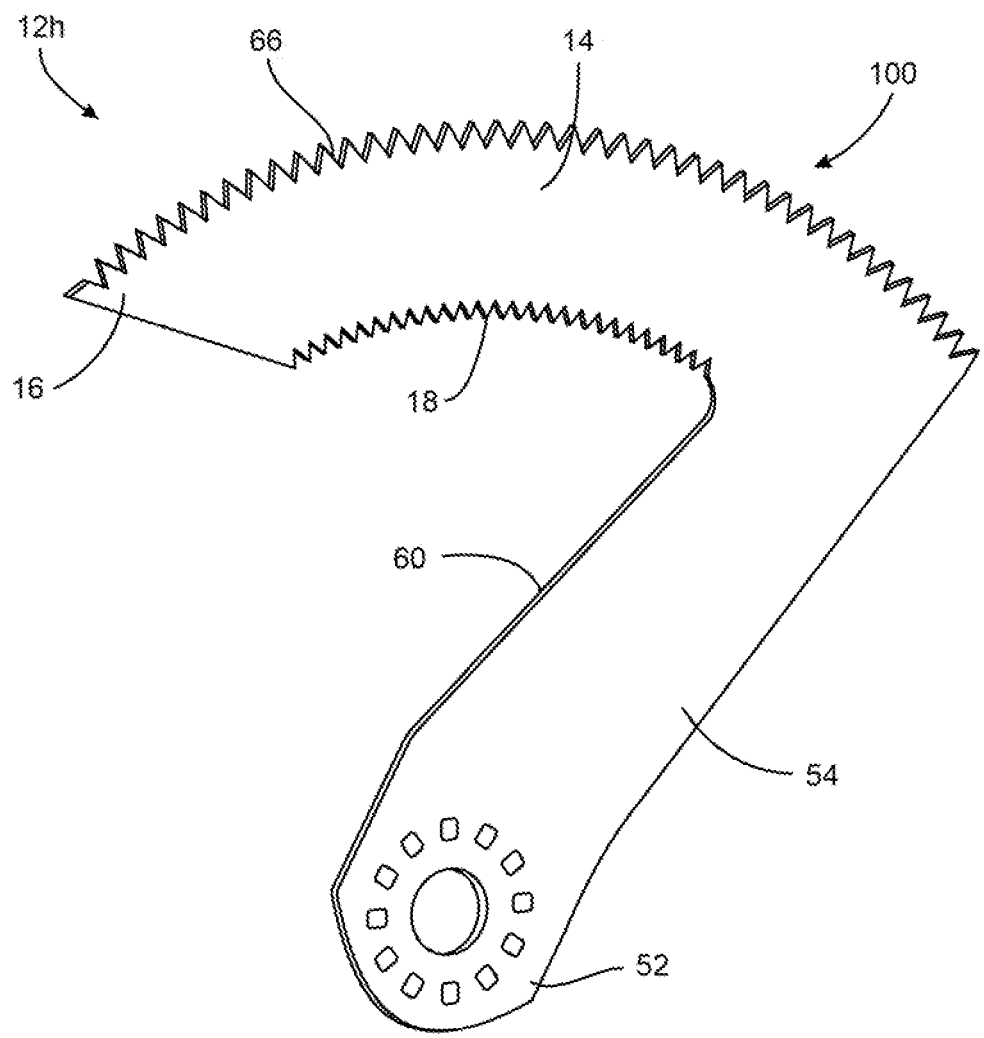

In the embodiment of FIGS. 1-10, only the trailing edge portion 18 of the blade 14 is configured as a cutting edge. FIG. 11 depicts an embodiment of a jab saw accessory tool in which both the leading and trailing edges 66, 18 of the blade 14 comprise cutting edges. The leading cutting edge 66 enables the accessory tool 12 to be used for "push" cutting by pushing the oscillating tool in the forward direction F so the leading cutting edge 66 cuts into an edge of the drywall. Thus, the jab saw accessory tools of FIG. 10 enables both "push" cutting and "pull" cutting operations to be performed with the same accessory tool. FIG. 11 also shows an alternative configuration of the tip portion 16. As depicted in FIG. 11, the tip portion 16 comprises a straight edge that extends between the outer cutting edge 66 and the inner cutting edge 18. The outer cutting edge 18 extends farther laterally than the inner cutting edge 66 which enables the tip portion 16 to taper to a point proximate the outer cutting edge 66. The straight edge of the tip portion 16 is a flat, razor sharp edge to facilitate penetration into drywall and similar materials.

In the embodiment of FIG. 11, the leading cutting edge 66 and the trailing cutting edge 18 each comprise a serrated edge. In alternative embodiments, the type of cutting edges and geometry of the cutting teeth can be the same or different for each cutting edge for use in different applications or with different kinds of materials. Other types of cutting edges that may be implemented for the cutting edges in any of the embodiments described herein include straight, flat cutting edges and abrasive cutting edges.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. An accessory for a power tool, comprising:
   a mounting portion configured to mate with an oscillating drive member of a power tool;
   a support arm portion extending forwardly from the mounting portion, the support arm portion including a first lateral edge that faces in a first lateral direction and a second lateral edge that faces in a second lateral direction; and
   a blade portion extending from the support arm portion generally in the first lateral direction, the blade portion including a trailing edge and a leading edge, the trailing edge extending from the first lateral edge in the first lateral direction and facing generally rearwardly toward the mounting portion, the leading edge extending from the second lateral edge generally in the first lateral direction and generally forwardly away from the mounting portion, the trailing edge and the leading edge portion meeting to define a tapered tip portion, the trailing edge and the leading edge portion meeting to define a tapered tip portion that is offset laterally from the support arm potion in the first lateral direction,
   wherein the first lateral edge of the support arm portion includes a lip portion, the lip portion extending linearly between a first position and a second position along the first lateral edge and having a planar outer surface that faces in the first lateral direction, and
   wherein the lip portion is located laterally outwardly of the mounting portion with respect to the first lateral direction.

2. The accessory tool of claim 1, wherein the lip portion is arranged generally perpendicular to the trailing edge of the blade portion.

3. The accessory tool of claim 1, wherein the lip portion is positioned on an offset portion of the first lateral edge, the offset portion being offset outwardly from the first lateral edge in the first lateral direction.

4. The accessory tool of claim 1, wherein the trailing edge includes a plurality of cutting teeth.

5. The accessory tool of claim 1, wherein the leading edge includes a plurality of cutting teeth.

6. The accessory tool of claim 1, wherein the leading edge and the trailing edge each include a plurality of cutting teeth.

* * * * *